US00PP29554P2

(12) United States Plant Patent
Donahue

(10) Patent No.: US PP29,554 P2
(45) Date of Patent: Jul. 31, 2018

(54) ***CLEMATIS* PLANT NAMED 'DONAHROS'**

(50) Latin Name: ***Clematis* hybrid**
Varietal Denomination: Donahros

(71) Applicant: Mark R. Donahue, Faribault, MN (US)

(72) Inventor: Mark R. Donahue, Faribault, MN (US)

(73) Assignee: DONAHUES GREEN HOUSES, INC, Faribault, MN (US)

( * ) Notice: Subject to any disclaimer, the term of this patent is extended or adjusted under 35 U.S.C. 154(b) by 63 days.

(21) Appl. No.: 14/999,558

(22) Filed: May 24, 2016

(51) Int. Cl.
*A01H 5/02* (2018.01)

(52) U.S. Cl.
USPC ..... Plt./228

(58) Field of Classification Search
USPC ..... Plt./228
See application file for complete search history.

*Primary Examiner* — Keith O Robinson
(74) *Attorney, Agent, or Firm* — Penny J. Aguirre

(57) ABSTRACT

A new cultivar of hybrid *Clematis*, 'Donahros', that is characterized by its flowers with six petals that emerge dark pink in color and fade to many shades of pink, its anthers that are burgundy in color, its dark green foliage, and its floriferous repeat bloom period beginning in June and then again in late August.

2 Drawing Sheets

Botanical classification: *Clematis* hybrid.
Variety denomination: 'Donahros'.

BACKGROUND OF THE INVENTION

The present invention relates to a new and distinct cultivar of *Clematis* of hybrid origin and will be referred to hereafter by its cultivar name 'Donahros'. 'Donahros' is an herbaceous perennial grown for use as a landscape plant, a flowering potted plant for the terrace, and as cut flower.

'Donahros' derived from an ongoing breeding program by the Inventor at his nursery in Faribault, Minn. The goal of the breeding program is to develop new cultivars of *Clematis* that exhibit heavy blooming habits. 'Donahros' was discovered by the Inventor as a chance seedling in his nursery trial garden in the summer of 2008. The new cultivar is most likely a seedling of open pollinated *Clematis* 'Pink Fantasy' (not patented) as the female parent and 'Kilian Donahue' (not patented) as the male parent.

Asexual propagation of the new cultivar was first accomplished by rooted cuttings under the direction of the Inventor in Faribault, Minn. in 2009. Asexual propagation has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Donahros' from other varieties of *Clematis*.

1. 'Donahros' exhibits flowers with six petals that emerge dark pink in color and fade to be many shades of pink.
2. 'Donahros' exhibits anthers that are burgundy in color.
3. 'Donahros' exhibits dark green foliage.
4. 'Donahros' exhibits a floriferous repeat bloom period beginning in June and then again in late August.

The female parent of 'Donahros', 'Pink Fantasy', differs from 'Donahros' in having flowers that are lighter pink in color, in having foliage that is darker green in color, and in having a later starting bloom period. The male parent of 'Donahros', 'Kilian Donahue', differs from 'Donahros' in having flowers that are both darker and lighter shades of pink in color, in having foliage that is darker green in color, in having a less vigorous growth habit, and in being less disease resistant. 'Donahros' can be most closely compared to the *Clematis* cultivar 'Hagley Hybrid' (not patented). 'Hagley Hybrid' differs from 'Donahros' in having flowers that are lighter pink-mauve in color, in having foliage that is blue-green in color, and in having a later starting and shorter lasting bloom period.

BRIEF DESCRIPTION OF THE DRAWINGS

The accompanying colored photographs illustrate the overall appearance and distinct characteristics of the new *Clematis*. The photographs were taken of a two year-old plant of 'Donahros' as grown outdoors in a trial garden in Faribault, Minn.

The photograph in FIG. 1 provides a side-view of a plant of 'Donahros' in bloom.

Figure 1:
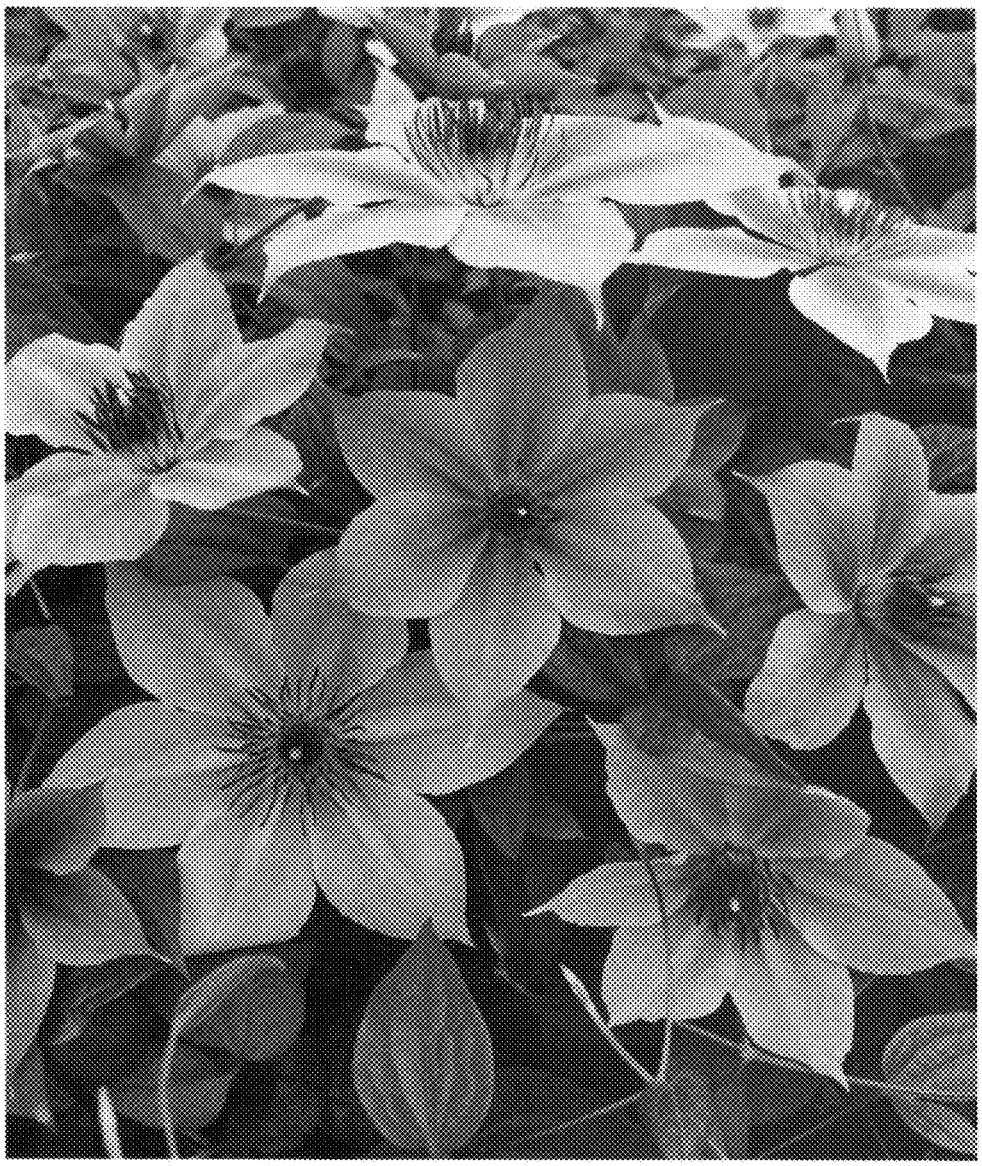
Figure 2:
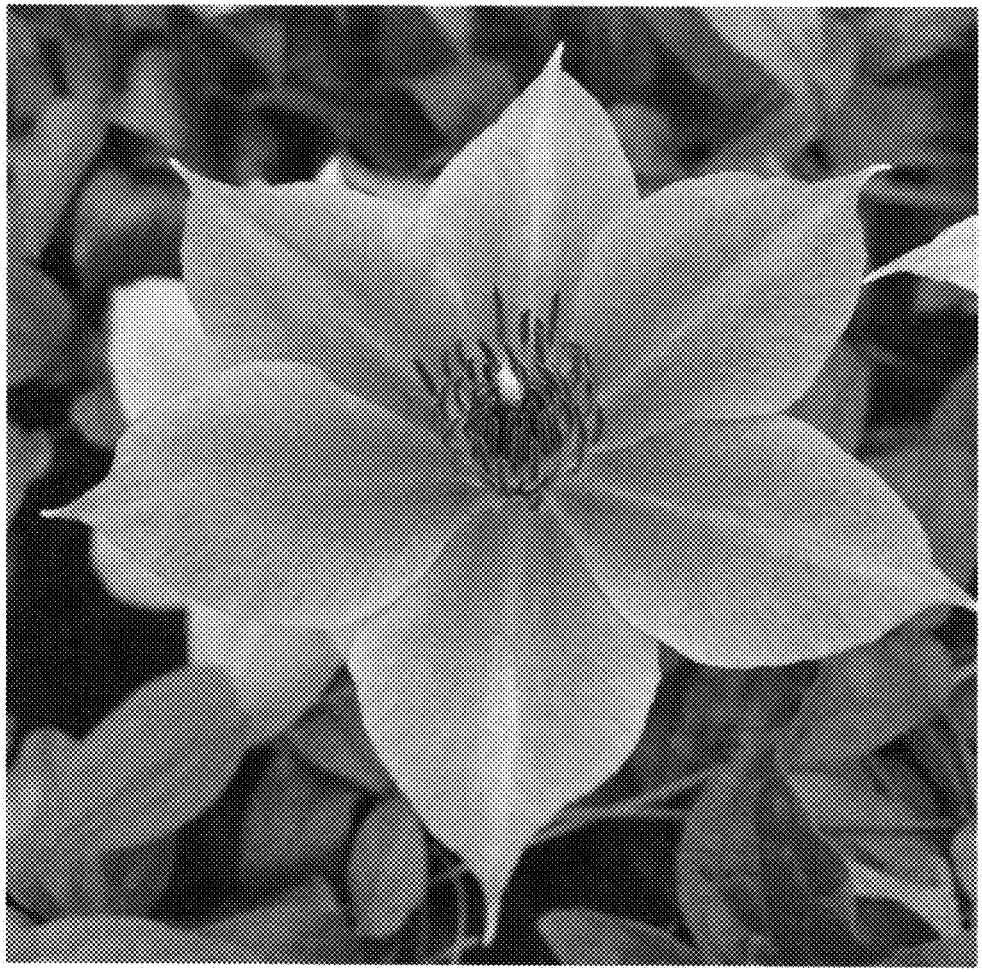

The photograph in FIG. 2 provides a close-up view of an inflorescence of 'Donahros'.

The colors in the photographs are as close as possible with the photographic and printing technology utilized and the color values cited in the detailed botanical description accurately describe the colors of the new *Clematis*.

DETAILED BOTANICAL DESCRIPTION

The following is a detailed description of two year-old plants of the new cultivar as grown outdoors in a trial garden in Faribault, Minn. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—In June and July and again in late August in Faribault, Minn., blooms on current year's growth.

*Plant type*.—Herbaceous perennial.

*Plant habit*.—Sub-climber.

*Height and spread*.—An average of 1.8 m in height (measured to the top of the flower) and 0.9 m in width.

*Cold hardiness*.—At least to U.S.D.A. Zone 4.

*Diseases and pests*.—No susceptibility or resistance to diseases and pests has been observed.

*Root description*.—Fleshy, 19C in color.

Growth and propagation:

*Propagation*.—Rooted cuttings.

*Time required for root development*.—An average of six weeks for root initiation with a rooted cutting produced after an average of three the four months.

*Growth rate*.—Very vigorous.

Stem description:

*Shape*.—Round and strongly 6-ribbed.

*Stem color*.—Young stems; ribs alternate in color between 159A and 199A, mature stems; become woody and alternate in color between 175A and 161A.

*Stem size*.—An average of 41 cm in length and 3 mm in diameter.

*Stem surface*.—Young stems; glossy and waxy to the touch, are moderately covered with tiny puberulent hairs that are slightly NN155A in color, up to 1 mm in length, mature stems; dull and waxy to the touch, moderately covered with tiny puberulent hairs that match the stem color, less than 0.5 mm in length, old stems at base; woody and dry.

*Stem strength*.—Young stems; flexible and strong, mature stems strong.

*Internode length*.—Ranges from 3 to 10 cm.

*Branching*.—Branching from the base.

Foliage description:

*Leaf arrangement*.—Opposite.

*Leaf division*.—Simple or ternate.

*Leaf size*.—An average of 7 cm in length and 4 cm in width.

*Leaf attachment*.—Petiolate.

*Leaf base*.—Cordate.

*Leaflet size*.—An average of 5 cm in length and 2.5 cm in width.

*Leaflet attachment*.—Petiolulate.

*Leaflet base*.—Ranging between cuneate and cordate.

*Leaflet/leaf shape*.—Lanceolate to broadly lanceolate.

*Leaflet/leaf apex*.—Acuminate.

*Leaflet/leaf fragrance*.—An astringent fragrance when crushed.

*Leaflet/leaf venation*.—Upper and lower surfaces reticulate, veins match the leaf surfaces and are moderately covered with tiny translucent puberulent hairs, less than 0.5 mm in length.

*Leaflet/leaf margin*.—Entire, moderately covered with tiny translucent puberulent hairs, less than 0.5 mm in length.

*Leaflet/leaf surface*.—Upper surface; glabrous and semi-glossy, lower surface; glabrous, semi-glossy and sparsely covered with tiny translucent puberulent hairs, less than 0.5 mm in length.

*Leaflet/leaf color*.—Upper and lower surface; 146A.

*Petioles*.—An average of 4 cm in length and 1 mm in diameter, young petiole color; 143B, mature petiole color; NN137A, base a blend of 149A, round in shape, strong, glossy and densely covered with puberulent hairs that match the surface color, up to 1 mm in length.

*Petiolules*.—Ranges between an average of 5 mm to 4 cm in length and 1 mm in diameter, young petiolule color; 143B, mature petiolule color; NN137A, base attachment a blend of 149A and 143B, round in shape, strong, glossy and moderately covered with puberulent hairs that match the surface color, up to 1 mm in length.

*Nodes*.—Surface is densely covered with long woolly hairs NN155A in color and up to 2 mm in length.

*Axillary buds*.—An average of 4 mm in length and 3 mm in width, surface is very densely covered with long tufts of woolly hair NN155A in color and up to 5 mm in length, when hairs fall off, the surface is glossy and glabrous.

Inflorescence description:

*Inflorescence type*.—Solitary or a 3 flowered dichasial cyme.

*Inflorescence arrangement*.—Terminal and axillary on young shoots.

*Peduncles*.—Up to 1.0 cm in length and up to 2 mm in width, color is 144A, surface slightly ribbed and moderately covered with tiny puberulent hairs that are slightly NN155A in color.

*Flower buds*.—Slightly drooping, lanceolate in shape, apex acuminate, base obtuse, a linear blend of 145B and 145C, surface is densely covered with woolly hairs that match the surface color and are up to 1.5 mm in length.

*Flower fragrance*.—Slight sweet fragrance.

*Lastingness of the flowers*.—Individual flowers last an average of 12 to 20 days.

*Flower quantity*.—Up to 50 flowers and buds on a mature plant.

*Flower type*.—Single, open campanulate to almost spreading.

*Flower aspect*.—Upright to outwards.

*Flower size*.—An average of 4 cm in diameter and 2 cm in depth.

*Tepal number*.—An average of 6.

*Tepal shape*.—Aristate.

*Tepal apex*.—Acuminate.

*Tepal base*.—Cuneate.

*Tepal margin*.—Entire, wavy.

*Tepal surface*.—Upper and lower surface; glabrous, satiny and very shiny, lower surface densely covered with short soft puberulent hairs matching the surface color, less than 0.5 mm in length.

*Tepal color*.—Upper (top) surface; center stripe a blend of N80A to 180B, edges blend outward from 84B to 84C, fused base 145A, lower surface (bottom); 84A, edges 84B, center stipe 4 mm in width, 145B in color.

*Tepal size*.—Up to 5.5 cm in length and 3 cm in width.

*Receptacle*.—7 mm in width and 4 mm in depth, N144A in color, densely covered with shiny hairs 157B in color and up to 1 mm in length.

Reproductive organs:

*Gynoecium*.—An average 60, an average of 3 cm in width and 0.5 mm in width, stigma is flattened ovate in shape, 155A in color, surface is shiny with a woolly hairs 155A in color; ovary is an average of 0.5 mm in diameter, 145B in color, densely cover puberulent.

*Androcoecium*.—An average of 50 to 70 stamens; basifixed anthers are flat and linear in shape, N77B in color, and up to 1.5 cm in length and 0.5 mm in width, filaments are 145D in color flushed with N80B near anther, short connective an average of 0.3 mm in length, pollen is low in quantity and 158C in color.

*Fruit and seed*.—Seed head is an average of 1.5 cm in length and 2 cm in width, a feather-like appearance en masse, style; plumose at base to mid section, very shiny surface, a blend of N199A and 196A, 1.4 cm in length, 1 mm in width, ovary an average of 1 mm in diameter, round in shape, very shiny surface, a blend of N200A and 191A in color.

It is claimed:

1. A new and distinct cultivar of *Clematis* plant named 'Donahros' as herein illustrated and described.

* * * * *